(12) United States Patent
Greiner et al.

(10) Patent No.: US 8,593,732 B1
(45) Date of Patent: Nov. 26, 2013

(54) PARTIALLY METALLIZED TOTAL INTERNAL REFLECTION IMMERSION GRATING

(75) Inventors: Christoph M. Greiner, Eugene, OR (US); Thomas W. Mossberg, Eugene, OR (US); Dmitri Iazikov, Eugene, OR (US)

(73) Assignee: LightSmyth Technologies, Inc., Eugene, OR (US)

( * ) Notice: Subject to any disclaimer, the term of this patent is extended or adjusted under 35 U.S.C. 154(b) by 162 days.

(21) Appl. No.: 13/012,796

(22) Filed: Jan. 24, 2011

Related U.S. Application Data

(60) Provisional application No. 61/297,732, filed on Jan. 23, 2010, provisional application No. 61/303,548, filed on Feb. 11, 2010.

(51) Int. Cl.
*G02B 5/30* (2006.01)
*G02B 27/28* (2006.01)

(52) U.S. Cl.
USPC .................................................. 359/485.05

(58) Field of Classification Search
USPC .......... 359/485.05, 487.03, 566–576; 362/19; 353/20
See application file for complete search history.

(56) References Cited

U.S. PATENT DOCUMENTS

| | | | |
|---|---|---|---|
| 4,490,440 A | 12/1984 | Reber | |
| 4,512,638 A * | 4/1985 | Sriram et al. | ................. 359/352 |
| 4,604,329 A | 8/1986 | Reber | |
| 4,725,511 A | 2/1988 | Reber | |
| 5,080,465 A | 1/1992 | Laude | |
| 5,377,044 A | 12/1994 | Tomono et al. | |
| 6,208,463 B1 | 3/2001 | Hansen et al. | |
| 6,426,837 B1 * | 7/2002 | Clark et al. | ............. 359/487.04 |
| 6,693,749 B2 * | 2/2004 | King et al. | .................... 359/630 |
| 6,813,080 B2 | 11/2004 | Raguin et al. | |
| 6,839,173 B2 | 1/2005 | Shimmo et al. | |
| 6,987,590 B2 | 1/2006 | Phillips et al. | |
| 8,270,079 B1 | 9/2012 | Mossberg et al. | |
| 2002/0191286 A1 | 12/2002 | Gale et al. | |
| 2004/0021945 A1 | 2/2004 | Tompkin et al. | |
| 2004/0196556 A1 | 10/2004 | Cappiello | |
| 2005/0088739 A1 | 4/2005 | Chiu et al. | |
| 2006/0274415 A1 * | 12/2006 | Murata | ........................ 359/486 |

(Continued)

OTHER PUBLICATIONS

Popov et al; "Backside diffraction by relief gratings"; Optics Communications vol. 65 No. 2, p. 97 (Jan. 15, 1988).

(Continued)

*Primary Examiner* — Stephone B. Allen
*Assistant Examiner* — Kimberly N Kakalec
(74) *Attorney, Agent, or Firm* — David S. Alavi

(57) ABSTRACT

A diffraction grating comprises a substrate with a set of protruding ridges and intervening trenches characterized by a ridge spacing $\Lambda$, width d, and height h. The substrate comprises a dielectric or semiconductor material with a refractive index $n_1$; the first substrate surface faces an optical medium with a refractive index $n_2$ that is less than $n_1$. Each ridge has a metal layer on its top surface of thickness t; at least a portion of the bottom surface of each trench is substantially free of metal. Over an operational wavelength range, $\lambda/2n_1 < \Lambda < \lambda/(n_1+n_2)$ can be satisfied. An optical signal can be incident on the diffractive elements from within the substrate at an incidence angle that exceeds the critical angle. The parameters $n_1$, $n_2$, $\Lambda$, d, h, and t can be selected to yield desired polarization dependence or independence of the diffraction efficiency.

30 Claims, 15 Drawing Sheets

(56) References Cited

U.S. PATENT DOCUMENTS

| | | |
|---|---|---|
| 2007/0146884 A1 | 6/2007 | Shiozaki et al. |
| 2009/0052030 A1* | 2/2009 | Kaida et al. .................. 359/486 |
| 2010/0277937 A1* | 11/2010 | Ilzuka et al. ................. 362/509 |
| 2011/0080640 A1* | 4/2011 | Kaida et al. .............. 359/485.05 |

OTHER PUBLICATIONS

Smith et al; "Diffraction gratings utilizing total internal reflection facets in Littrow configuration"; IEEE Photonics Technology Letters vol. 11 No. 1, p. 84 (Jan. 1999).

U.S. Appl. No. 13/622,339, filed Sep. 18, 2012, Mossberg et al.

\* cited by examiner

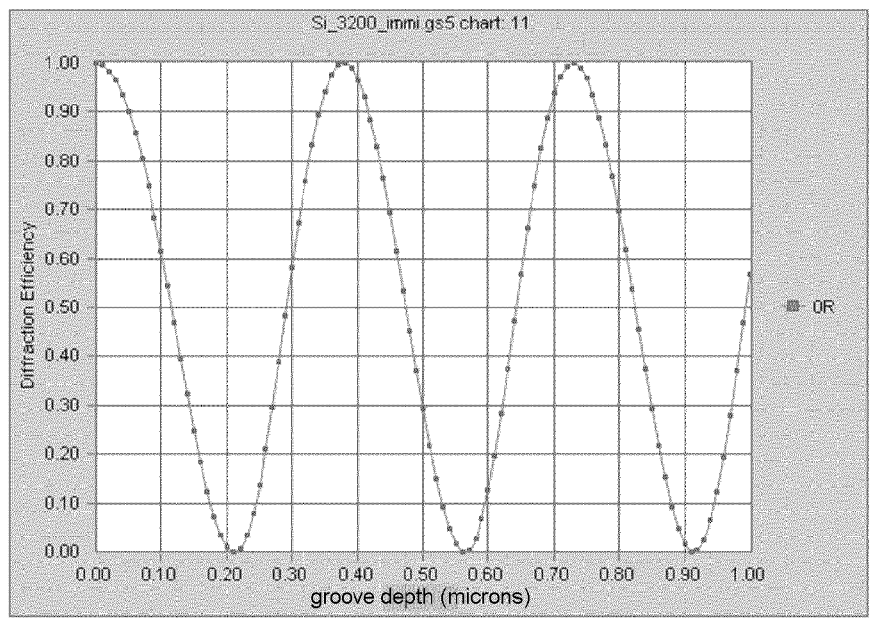
FIG. 4A  0th order
s-pol
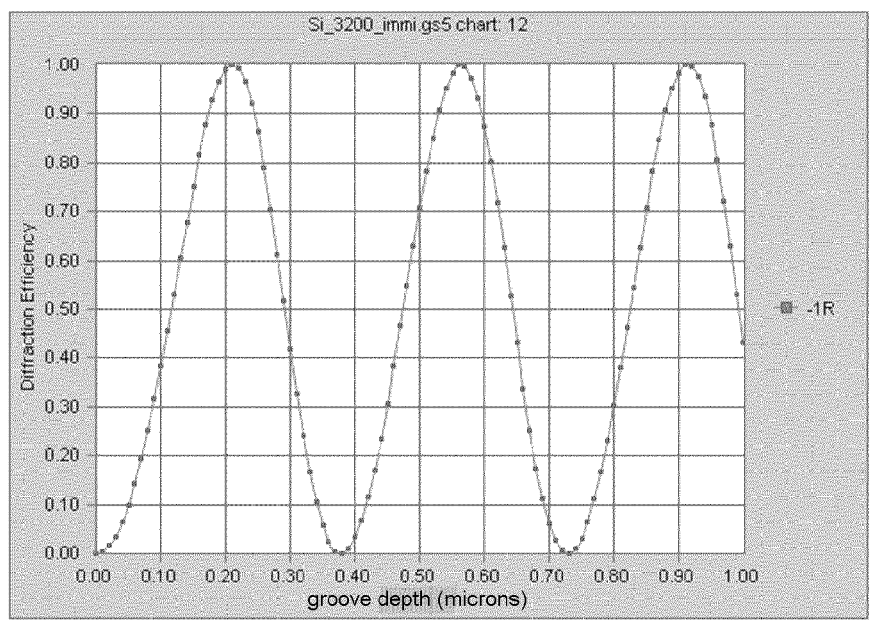
FIG. 4B  1st order
s-pol

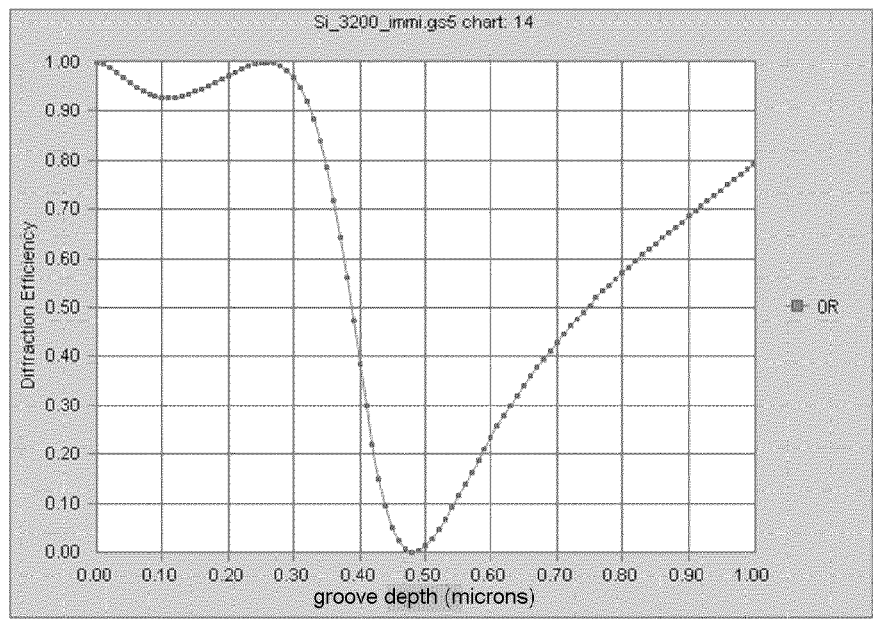
FIG. 5A  0th order p-pol
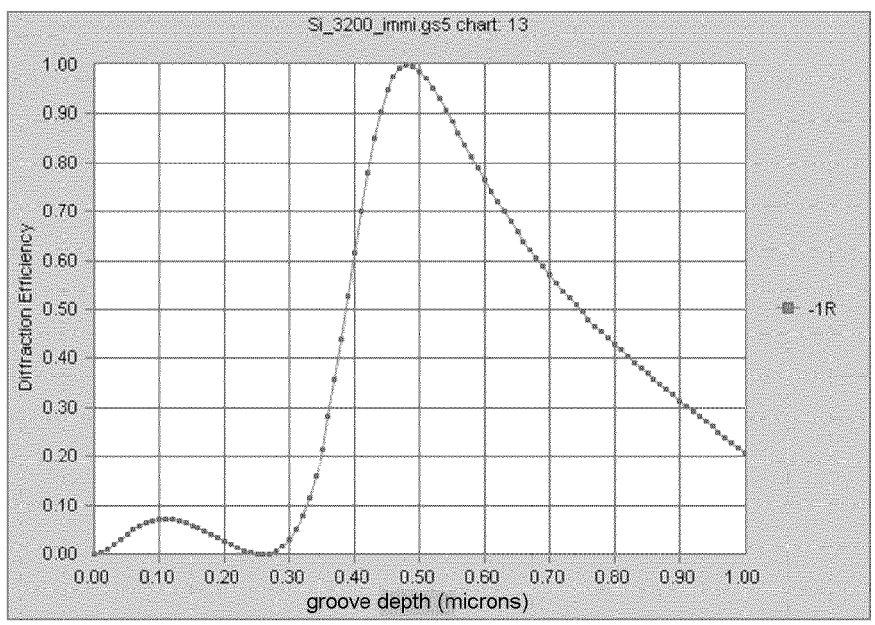
FIG. 5B  1st order p-pol

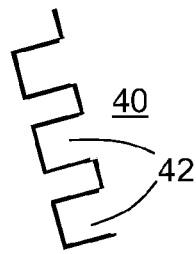
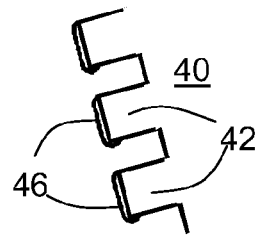
FIG. 13A
FIG. 13B
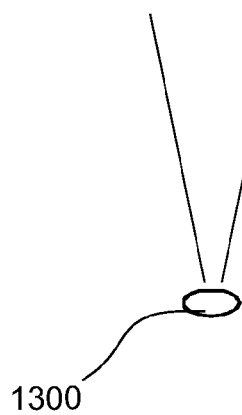
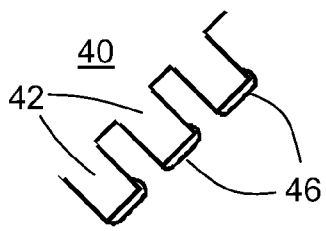
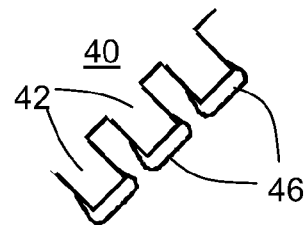
FIG. 13C
FIG. 13D
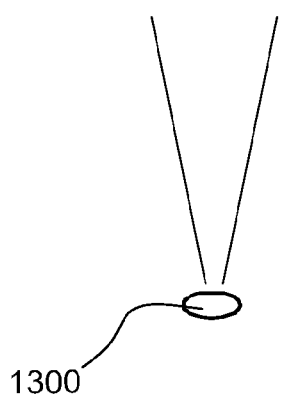

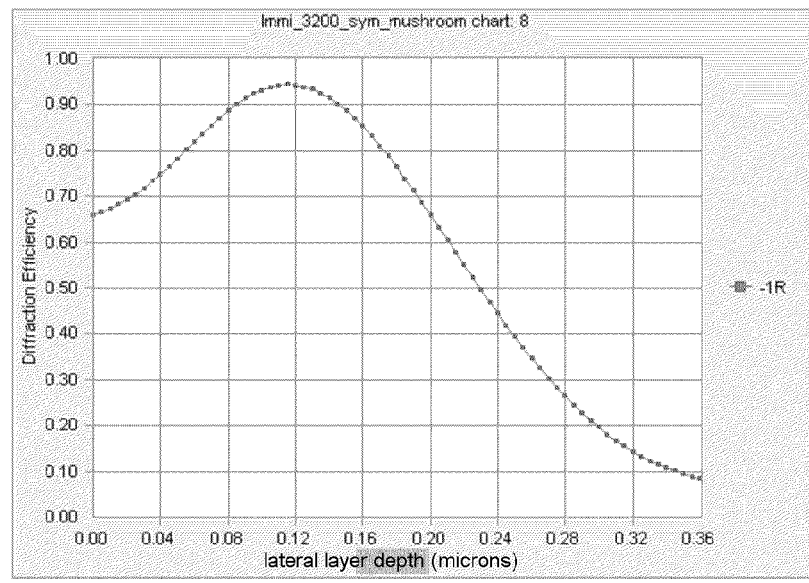
FIG. 15B  1st order
s-pol
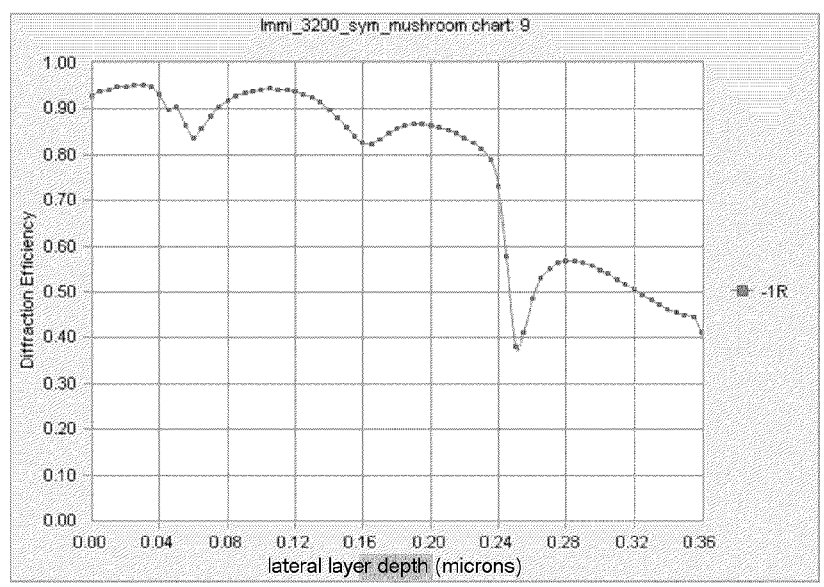
FIG. 15C  1st order
p-pol

US 8,593,732 B1

PARTIALLY METALLIZED TOTAL INTERNAL REFLECTION IMMERSION GRATING

BENEFIT CLAIMS TO RELATED APPLICATIONS

This application claims benefit of (i) U.S. provisional App. No. 61/297,732 entitled "Highly Efficient Reflection Immersion Gratings" filed Jan. 23, 2010 in the names of Christoph M. Greiner, Thomas W. Mossberg, and Dmitri Iazikov, and (ii) U.S. provisional App. No. 61/303,548 entitled "Highly Efficient Reflection Immersion Gratings" filed Feb. 11, 2010 in the names of Christoph M. Greiner, Thomas W. Mossberg, and Dmitri Iazikov. Both of said provisional applications are incorporated by reference as if fully set forth herein.

BACKGROUND

The field of the present invention relates to optical diffraction gratings. In particular, partially metalized total internal reflection immersion gratings and methods of fabricating the same are disclosed herein.

Examples of immersion gratings are described in:

Popov et al, "Backside diffraction by relief gratings," Optics Communications Vol. 65 No. 2, p. 97 (15 JAN 1988);

Smith et al, "Diffraction gratings utilizing total internal reflection facets in Littrow configuration," IEEE Photonics Technology Letters Vol. 11 No. 1, p. 84 (JAN 1999); and U.S. Pat. No. 6,813,080 entitled "Metal-free gratings for wavelength-multiplexed optical communications" issued Nov. 2, 2004 to Raguin et al.

SUMMARY

A diffraction grating comprises a substrate with a set of diffractive elements formed on its surface. The diffractive elements comprise a set of protruding ridges separated by intervening trenches characterized by a ridge spacing $\Lambda$, a ridge width d, and a ridge height h. The substrate comprises a dielectric or semiconductor material substantially transparent over a range of operational wavelengths $\lambda$ with a refractive index $n_1$; the first substrate surface faces an optical medium with a refractive index $n_2$ that is less than $n_1$. Each ridge has a metal layer on its top surface that is characterized by a thickness t; at least a portion of the bottom surface of each trench is substantially free of metal. Over the operational wavelength range, $\lambda/2n_1 < \Lambda < \lambda/(n_1+n_2)$ can be satisfied. The substrate can be arranged so that an optical signal is incident on the diffractive elements from within the substrate (i.e., the diffraction grating is a so-called immersion grating) at an incidence angle that exceeds the critical angle. The parameters $n_1$, $n_2$, $\Lambda$, d, h, and t can be selected to yield desired polarization dependence or independence of the diffraction efficiency.

Objects and advantages pertaining to diffraction gratings, including immersion gratings, may become apparent upon referring to the exemplary embodiments illustrated in the drawings and disclosed in the following written description or appended claims.

BRIEF DESCRIPTION OF THE DRAWINGS

FIGS. 4A and 4B are calculated plots of zeroth and first order s-polarized diffraction efficiencies, respectively, as a function of ridge height h for the grating of FIG. 3.

FIGS. 5A and 5B are calculated plots of zeroth and first order p-polarized diffraction efficiencies, respectively, as a function of ridge height h for the grating of FIG. 3.

FIGS. 13A-13D illustrate schematically an exemplary process for depositing a metal layer on the grating ridges.

FIGS. 15B and 15C are calculated plots of s- and p-polarized first order diffraction, respectively, as a function of lateral metal layer depth a for the grating of FIG. 15A.

Figure 1:
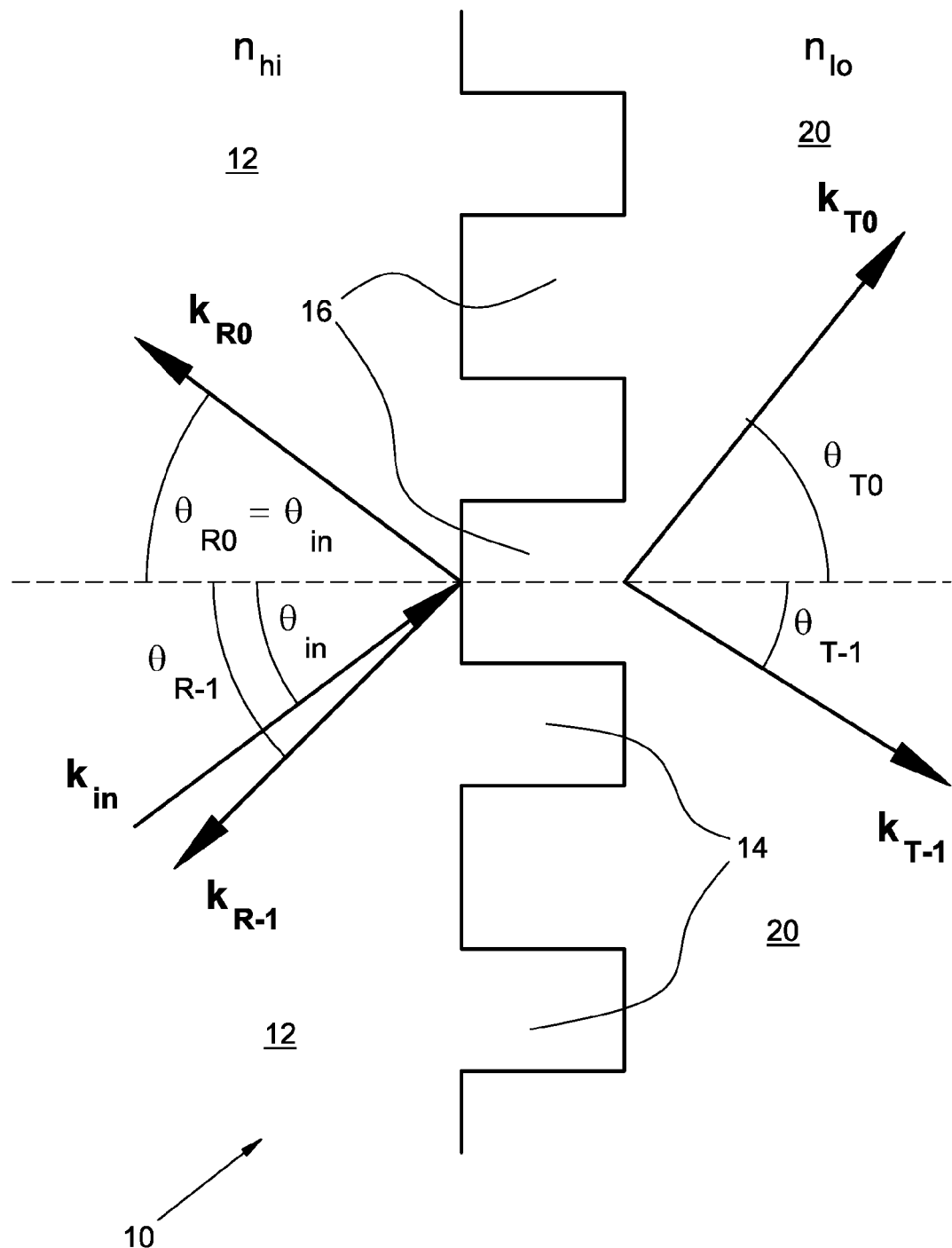
FIG. 1 illustrates schematically an exemplary diffraction grating used as an immersion grating.

It should be noted that the embodiments depicted in this disclosure are shown only schematically, and that not all features may be shown in full detail or in proper proportion. Certain features or structures may be exaggerated relative to others for clarity. For example, the actual optical gratings depicted as having a handful of diffractive lines or ridges typically have hundreds or thousands of lines per millimeter. The number of lines is reduced in the drawings for clarity. It should be noted further that the embodiments shown are exemplary only, and should not be construed as limiting the scope of the written description or appended claims.

DETAILED DESCRIPTION OF EMBODIMENTS

FIG. 1 illustrates schematically a cross sectional view of a conventional diffraction grating 10. The cross section is substantially perpendicular to the grating lines, which in this example comprise ridges 14 and intervening trenches 16 on a first surface of a substrate 12. The ridges are shown as rectangular in cross section, but this need not be the case; other ridge shapes can be employed, e.g., trapezoidal, triangular, sinusoidal, and so forth. The substrate 12 comprises a material having a refractive index $n_{hi}$. The diffraction grating can be characterized by a grating spacing $\Lambda$, and the first substrate surface faces an optical medium 20 having a refractive index with $n_{lo} < n_{hi}$. The substrate material and optical medium are substantially transparent within the spectral range of interest (i.e., over an operational range of wavelengths $\lambda$). In a common arrangement, the optical medium 20 comprises ambient air or other gaseous medium; any suitable solid, liquid, or gaseous material, or vacuum, can be employed as the optical medium. Any suitable substrate material can be employed; common examples include optical glass, fused silica, silicon, silicon nitride, silicon oxynitride, aluminum oxide (sapphire), various polymers, other dielectric or semiconductor materials, and so forth.

In FIG. 1, an optical signal with wave vector $k_{in}$ and vacuum wavelength in incident on the grating 10 from within the substrate 10 (i.e., from the high index side of the grating, so that grating 10 can be referred to as an immersion grating). The optical signal is incident at incidence angle $\theta_{in}$ with respect to the grating normal. In the example of FIG. 1, $n_{lo}$, $n_{hi}$, and $\Lambda$ are chosen so that only one transmitted and one reflected diffraction order are present (in addition to the transmitted and reflected zero order optical signals). In addition, in FIG. 1, $\theta_{in} < \theta_c$, where $\theta_c$ is the critical angle beyond which total internal reflection occurs (i.e., $\theta_c = \sin^{-1}(n_{lo}/n_{hi})$). Under the conditions of FIG. 1, the immersion grating 10 (i) diffracts a transmitted optical signal (transmitted negative first order, wave vector $k_{T-1}$) that exits the grating with angle $\theta_{T-1}$, (ii) refracts a zeroth order transmitted optical signal with wave vector $k_T$, (iii) diffracts a reflected optical signal (reflected negative first order, wave vector $k_{R-1}$) that back diffracts with angle $\theta_{R-1}$, and (iv) reflects a zeroth-order reflected optical signal with wave vector $k_{Ro}$ (specular reflection). Angle $\theta_{T-1}$ is related to $\theta_{in}$ by the law of refraction; angles $\theta_{T-1}$ and $\theta_{R-1}$ are related to $\theta_{in}$ by the grating equation.

For many applications, e.g., optical signal transmission, it is desirable for the diffraction grating to diffract incident optical signals with relatively high efficiency (e.g., >80% or >90%) over a substantial spectral range (e.g., about 1500-1600 nm) into only a single diffraction order, so as to avoid unnecessary optical loss. The presence of undesirable energy output pathways such as specular reflection, non-diffracted transmission, and undesired diffraction orders, can make it difficult to design a diffraction grating with sufficiently high efficiency of diffraction into only the desired diffraction order or with a sufficiently broad spectral range of high diffraction efficiency. Consequently, it can be beneficial to eliminate undesirable energy output pathways so as to enable reduction of optical loss in the desired diffracted order.

Figure 2:
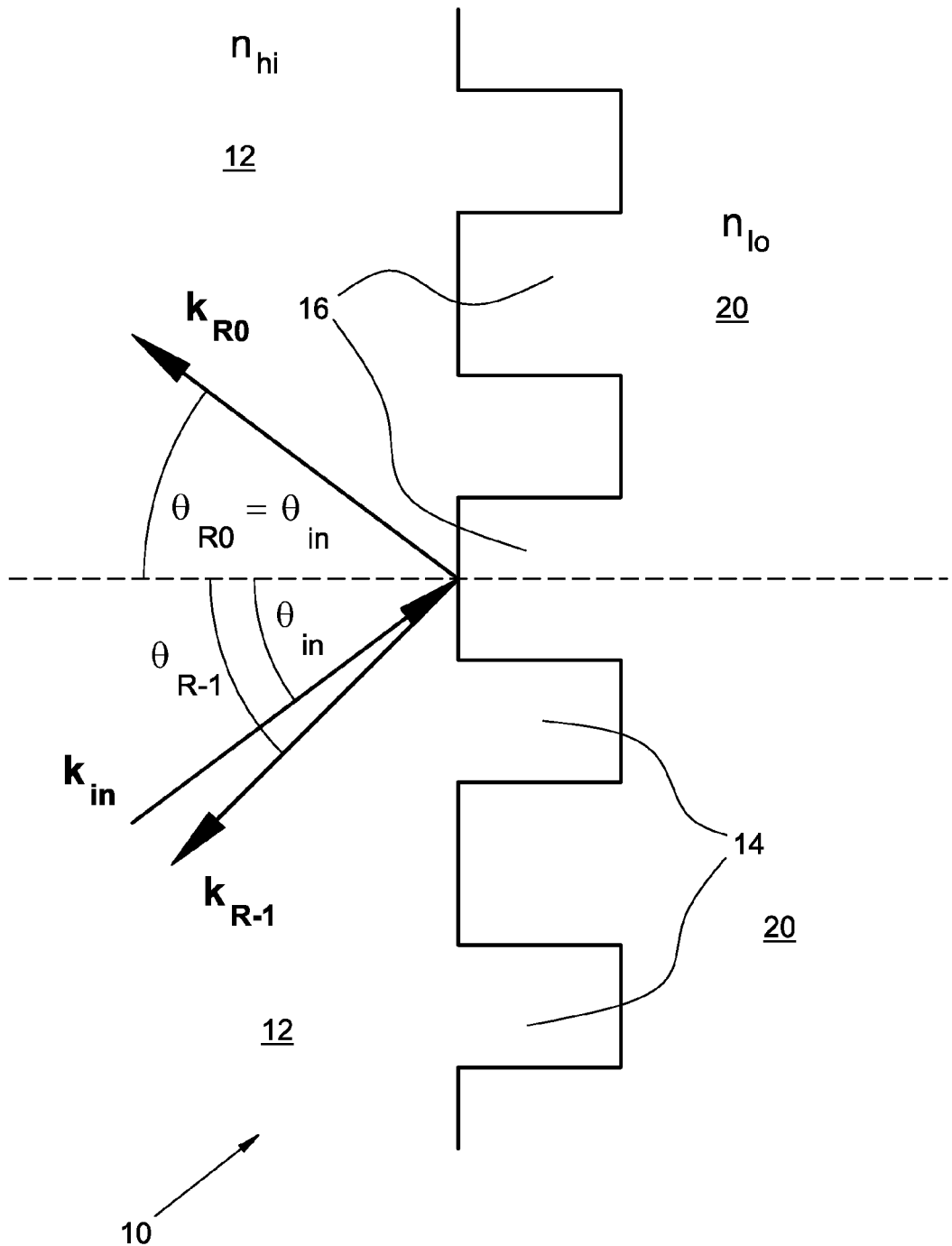
FIG. 2 illustrates schematically an exemplary diffraction grating used as an immersion grating in a total internal reflection arrangement.

An example of elimination of transmitted output pathways (refracted and diffracted) is illustrated schematically in FIG. 2. The grating spacing $\Lambda$ has been chosen so that, for an incident optical signal of wavelength $\lambda$, (i) $\Lambda < \lambda/(n_{lo}+n_{hi})$ and (ii) $\lambda/2n_{hi} < \Lambda$. Condition (i) implies that, for an optical signal incident from the high index side of the diffraction grating 10, no diffraction into the low index medium can occur and diffracted orders higher than the first diffracted order are absent within the high index medium. Condition (ii) implies that first order diffraction within the high index medium is possible. Additionally, if the incidence angle is larger than the critical angle (i.e., if $\theta_{in} > \theta_c$, with $\theta_c = \sin^{-1}(n_{lo}/n_{hi})$), then no zeroth-order transmission can occur and the input optical signal undergoes total internal reflection. Under those conditions, the only remaining output pathways are (i) the reflective zeroth order (i.e., specular total internal reflection) and (ii) the first order reflective diffraction, both of which occur within the high index medium 12. By suitably arranging the morphology of the diffraction grating, nearly 100% of the incident optical signal energy can be directed into the first diffraction order; various examples of such arrangements of grating morphology are demonstrated in the following disclosed exemplary embodiments.

Figure 3:
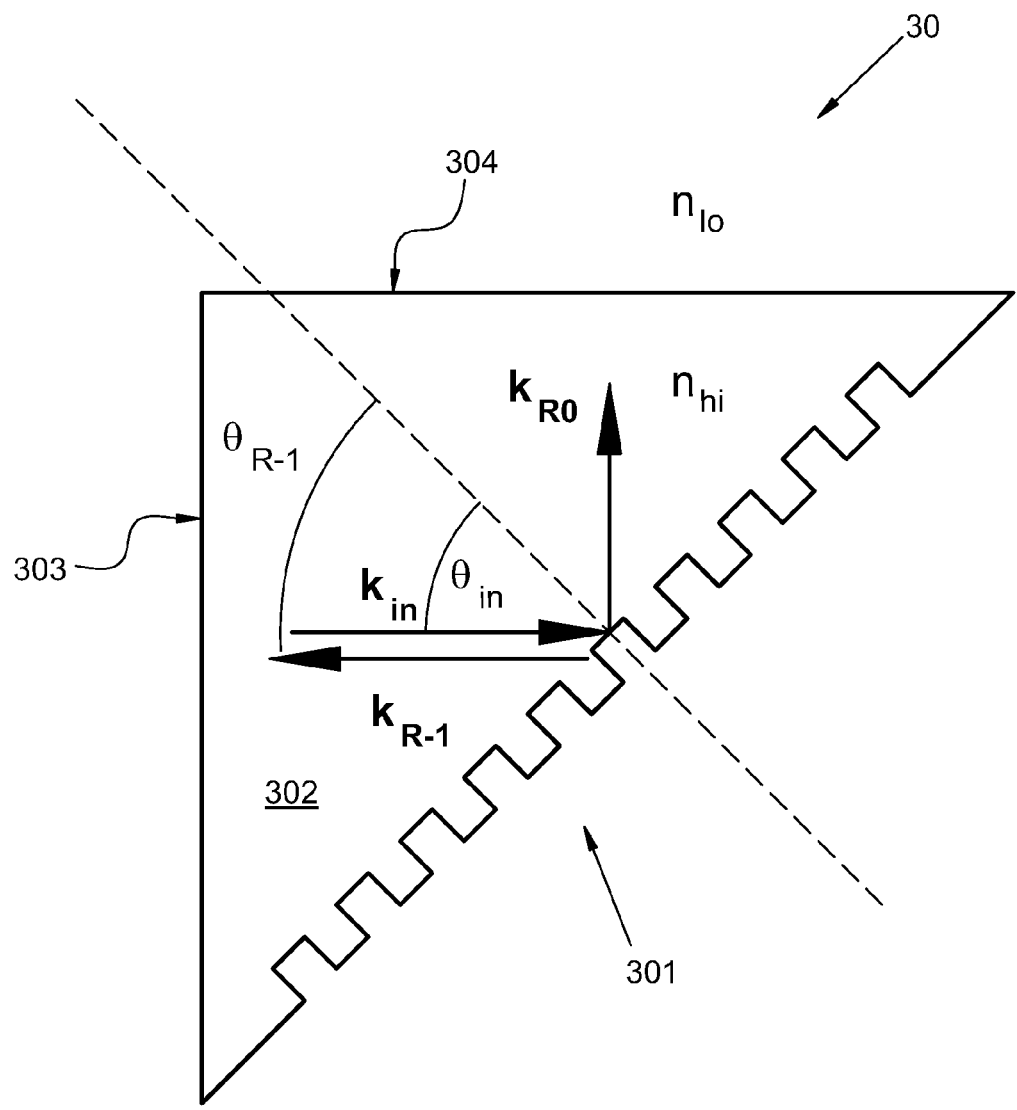
FIG. 3 illustrates schematically an exemplary diffraction grating formed on a prism surface and used as an immersion grating.

FIG. 3 illustrates schematically an exemplary silicon immersion grating 30, which has a diffraction grating 301 formed as a surface corrugation on one surface of a silicon prism substrate 302. The grating 301 can be fabricated directly on the prism-shaped substrate 302, or on a discrete silicon substrate (e.g., a piece of standard silicon wafer) that is subsequently bonded to the prism substrate 302 by optical contacting or other suitable method. Although shown as a right-angled prism, any suitable or desired prism shape can be employed; prism angles can be chosen for convenience provided that refraction of an incident optical signal into the prism results in the desired angle of incidence onto the diffraction grating 301. The grating period is $\Lambda = 312.5$ nm in this example. The index of silicon is $n_{hi} = 3.5$ and the prism is surrounded by ambient air with $n_{lo} = 1$.

An optical signal is incident on the immersion grating 301 from within the substrate 302, at a designed incidence angle $\theta_{in}$, with wave vector $k_{in}$ and vacuum wavelength $\lambda = 1.545$ μm. The incident optical signal can preferably propagate in a direction normal to the prism entrance face 303, but any incidence angle on the prism entrance face 303 can be employed that refracts the optical signal to propagate along the desired angle of incidence $\theta_{in}$ on the immersion grating 301. Undesirable reflection loss at surface 303 can be reduced to an operationally acceptable level by an antireflection coating of any suitable type or arrangement, if needed or desired. The incident optical signal propagates within the silicon substrate 302, impinges on the grating 301, and is back diffracted with wave vector $k_{R-1}$ at a diffraction angle $\theta_{R-1}$. In the example of FIG. 3 the diffraction takes place near the Littrow condition (i.e., $\theta_{in} = \theta_{R-1}$), however, any suitable combination of $\theta_{in}$ and $\theta_{R-1}$ can be employed (within the constraints of the grating equation, of course), including non-Littrow arrangements. Suitable arrangement of the duty cycle and trench depth can be employed to concentrate the optical output of the grating 301 into a designed output channel in both Littrow and non-Littrow arrangements, as disclosed further herein.

The grating incidence angle $\theta_{in}$ is 45.3° (near-Littrow condition) with respect to the grating normal in the example of FIG. 3. For an immersion grating 301 on a silicon substrate in air, $n_{hi} = 3.5$, $n_{lo} = 1$, and the critical angle $\theta_c = 16.6°$ (with respect to the grating normal). Since $\theta_{in} > \theta_c$ in this example, no zeroth order transmission is present. Additionally, since $\Lambda < \lambda/(n_{hi}+n_{lo})$, no transmitted diffracted orders are present on the air side of the immersion grating 301, and no reflected diffracted order higher than first order is present on the silicon side of the immersion grating 301. Within the silicon prism substrate 302, since $\lambda/2n_{hi} < \Lambda$, the first reflected diffracted order can be present, and only the zeroth and first orders share the energy of the incident optical signal after it interacts with the immersion grating 301.

FIGS. 4A and 4B show the efficiency as a function of ridge height h (equivalently, trench or groove depth) of zero order (FIG. 4A) and first order (FIG. 4B) diffraction orders within the silicon prism substrate of FIG. 3. The efficiencies plotted in FIGS. 4A and 4B were calculated for a duty cycle $d/\Lambda = 0.425$ (where d is the width of the rectangular ridges that constitute the grating, or the average width of non-rectangular ridges) and for s-polarization of the incident optical signal (i.e., electric field vector parallel to the lines of the grating 301). As can be seen in FIGS. 4A and 4B, at certain groove depths, nearly 100% calculated diffraction efficiency can be achieved into the first diffracted order, while nearly 100% calculated reflection (i.e., diffraction into the zero order) can be achieved at other groove depths; those variations are roughly oscillatory and complementary (i.e., the first order diffraction goes through a maximum at a ridge height where the zero order reflection goes through a minimum, and vice versa); the first order diffraction goes through maxima at groove depths of about 210 nm, about 560 nm, and about 910 nm. FIGS. 5A and 5B show calculated efficiency as a function of ridge height h for a p-polarized input optical signal (zeroth order in FIG. 5A; first order in FIG. 5B), with all other conditions being the same as in FIGS. 4A and 4B. Over the range of ridge heights h shown, the efficiencies are complementary, but not oscillatory; the first order diffraction goes through a single maximum at a groove depth of about 490 nm in this example.

Figure 6A:
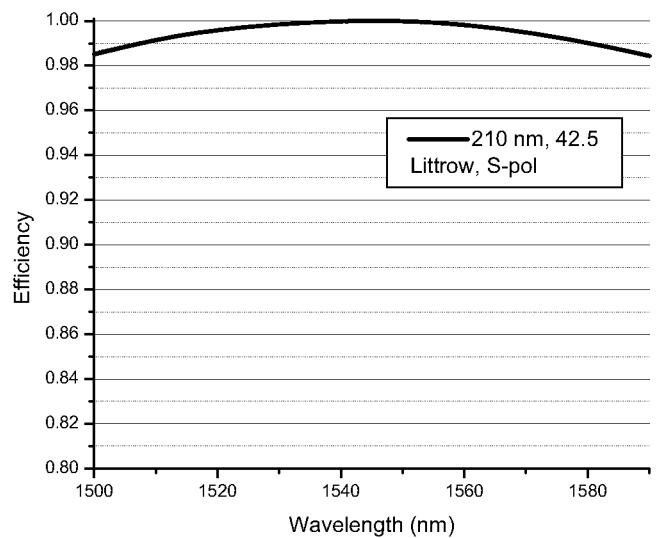
FIG. 6A is a calculated plot of first order s-polarized diffraction efficiency as a function of wavelength for the grating of FIG. 3.
Figure 6B:
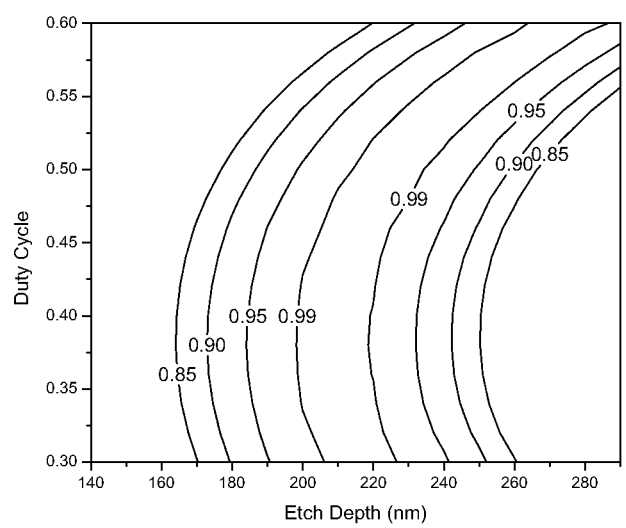
FIG. 6B is a calculated plot of first order s-polarized diffraction efficiency as a function of ridge height h and duty cycle d/$\Lambda$ for the grating of FIG. 3.

The ridge height h can be used as an adjustable parameter to design a diffraction grating that exhibits near unity calculated first order diffraction efficiency for a specified combination of $n_{hi}$, $n_{lo}$, $\lambda$, $\Lambda$, d, and polarization, as shown in FIGS. 4B and 5B. For example, FIG. 6A is a plot of first order diffraction efficiency of an s-polarized optical signal for the immersion grating of FIG. 3 with d/$\Lambda$=0.425 and h=210 nm. Greater than 98% diffraction efficiency is calculated over a spectral range of about 1500-1590 nm. FIG. 6B is a contour plot indicating how the first order efficiency at $\lambda$=1545 nm depends on grating morphology parameters, i.e., groove depth h and duty cycle d/$\Lambda$, near the optimal duty cycle (0.425) and groove depth (210 nm). High first order diffraction efficiency can be expected over a relatively large variation of groove depth and duty cycle, making the immersion grating 301 relatively insensitive to inevitable fabrication-induced variations of those grating parameters. Actual diffraction efficiencies of fabricated gratings can be less than those calculated, however, the parameters calculated to yield near unity diffraction efficiency typically yield near maximal measured diffraction efficiency achieved by a grating fabricated according to those parameters.

By choosing a suitable value for h, an immersion grating 301 can be designed that diffracts both s- and p-polarized optical signals with substantially similar efficiencies (i.e., the grating exhibits so-called polarization dependent loss (PDL) at or below an operationally acceptable level). For example, in the example of FIG. 3, maximum first order diffraction efficiency is obtained at a groove depth h of about 490 nm for p-polarization and about 560 nm for s-polarization. An immersion grating with similarly highly efficient first order diffraction for both polarizations simultaneously can be designed, for example, by choosing a groove depth h that is an average of the optimal depths for the individual polarizations (e.g., 525 nm in this example).

Figure 7:
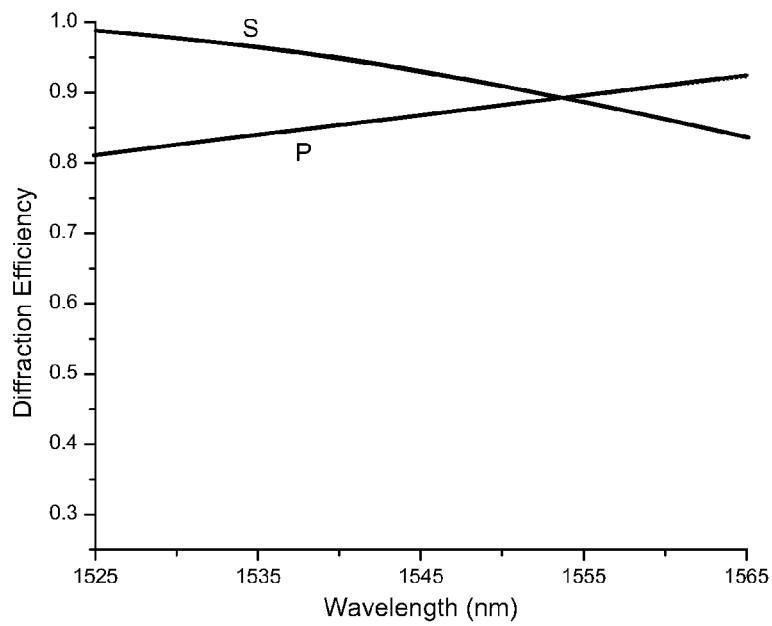
FIG. 7 is a calculated plot of s- and p-polarized first order diffraction efficiency as a function of wavelength for the grating of FIG. 3.

Varying the duty cycle d/$\Lambda$ shifts the maximum of the p-polarized first order diffraction efficiency relative to the maxima of the s-polarized first order diffraction efficiency in the plots of FIGS. 4A, 4B, 5A, and 5B. By choosing a suitable combination of h and d, the maximum of the p-polarized first order diffraction can be made to substantially coincide with a maximum of the s-polarized first order diffraction, yielding an immersion grating with low PDL. FIG. 7 shows the efficiency for s- and p-polarized optical signals calculated for an immersion grating with parameters identical to the previous example except that d/$\Lambda$=0.5 and h=570 nm. Over the telecom C-band (i.e., $\lambda$ between about 1525 nm and about 1565 nm), greater than 80% first order diffraction efficiency is calculated for both polarizations, and the polarization-dependent loss (PDL) is less than 1 dB across that operational wavelength range.

A duty cycle d/$\Lambda$ can be selected so that a maximum efficiency of s-polarized first order diffraction (with respect to trench depth h) substantially coincides with a minimum efficiency of p-polarized first order diffraction, or vice versa. The resulting immersion grating exhibits polarization selectivity, diffracting the s-polarized component of an incident optical signal into the first diffracted order while specularly reflecting the p-polarized component of the incident optical signal (or vice versa). Such a polarization selective grating can be used to separate or combine orthogonally polarized optical signal components. Polarization ratios of up to about 100:1 or more can be achieved, for example; lesser polarization ratios can be usefully employed.

Figure 8:
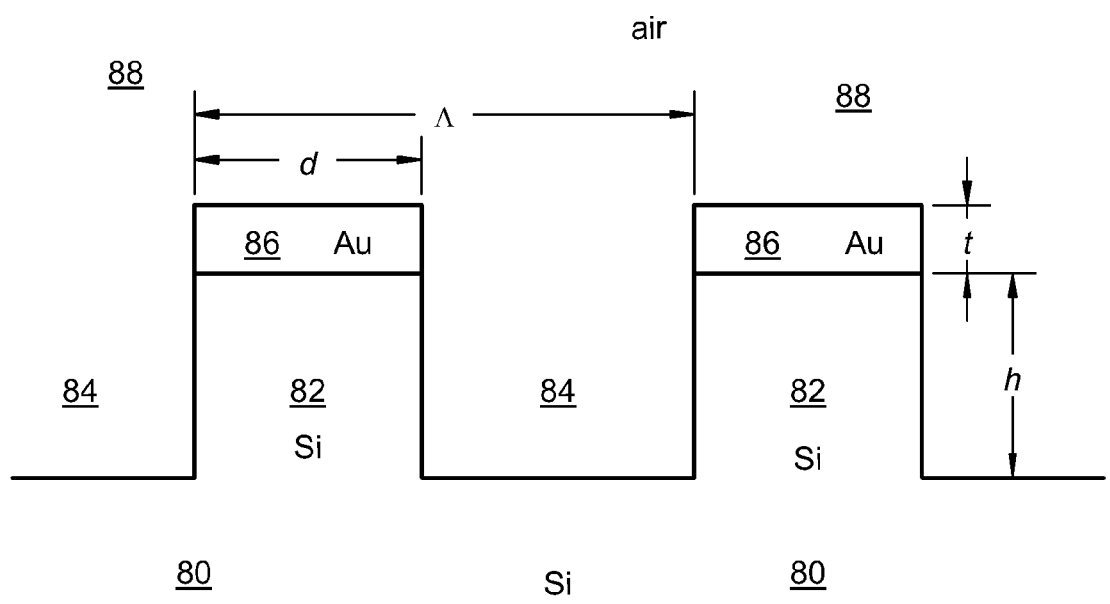
FIG. 8 illustrates schematically an exemplary diffraction grating with a metal layer on each grating ridge.

In another exemplary embodiment illustrated schematically in FIG. 8, the top surface of each grating ridge 82 (also referred to as grating teeth, mesas, or posts, due to their appearance in cross section) is covered with a metal layer 86 of thickness t (gold in this example). The bottom surface of each trench 84 is left substantially free of metal. In the example of FIG. 8, the grating is formed on a silicon substrate 80 and faces an optical medium 88 of ambient air; the ridge height h is 285 nm and the thickness t is 50 nm. As in the previous example, the grating line density is 3200 lines/mm, i.e., the grating period $\Lambda$ is 312.5 nm. An optical signal with $\lambda$=1545 nm is incident on the grating from within the substrate 80 with $\theta_{in}$=45.3° (near-Littrow condition). A simulation based on the rigorous coupled-wave approximation indicates that the grating structure of FIG. 8 will exhibit about 97% efficiency for s-polarized first order diffraction.

The thickness t of the metal layer 86 can be used as an additional design parameter. By choosing appropriate values for $n_1$, $n_2$, $\Lambda$, d, h, and t, one can design diffraction gratings that are similarly highly efficient for both input polarizations, i.e., to reduce, minimize, or eliminate polarization dependence of the first order diffraction efficiency over an operational wavelength range and achieve polarization dependent loss (PDL) at or below an operational acceptable level. Alternatively, $n_1$, $n_2$, $\Lambda$, d, h, and t can be chosen to design immersion gratings that are polarization selective, i.e., highly efficient first order diffraction for one polarization and highly efficient specular zero order reflection for the other polarization. It should be noted that metal deposition processes used to form the metal layer 86 may not yield a layer of uniform thickness. Such non-uniform layers nevertheless result in the behavior disclosed herein, and shall fall within the scope of the present disclosure or appended claims. In the case of a non-uniform metal layer 86, the thickness t that characterizes the layer can be an average thickness or a maximum thickness, for example.

Figure 9A:
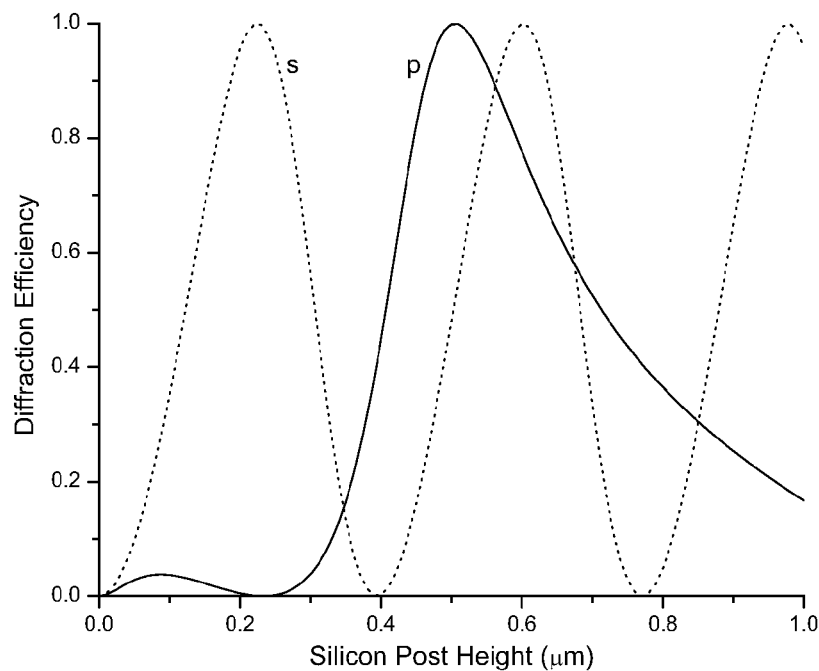
FIGS. 9A-9D are calculated plots of s- and p-polarized first order diffraction efficiencies as a function of ridge height h for various metal layer thickness t for the grating of FIG. 8.
Figure 9B:
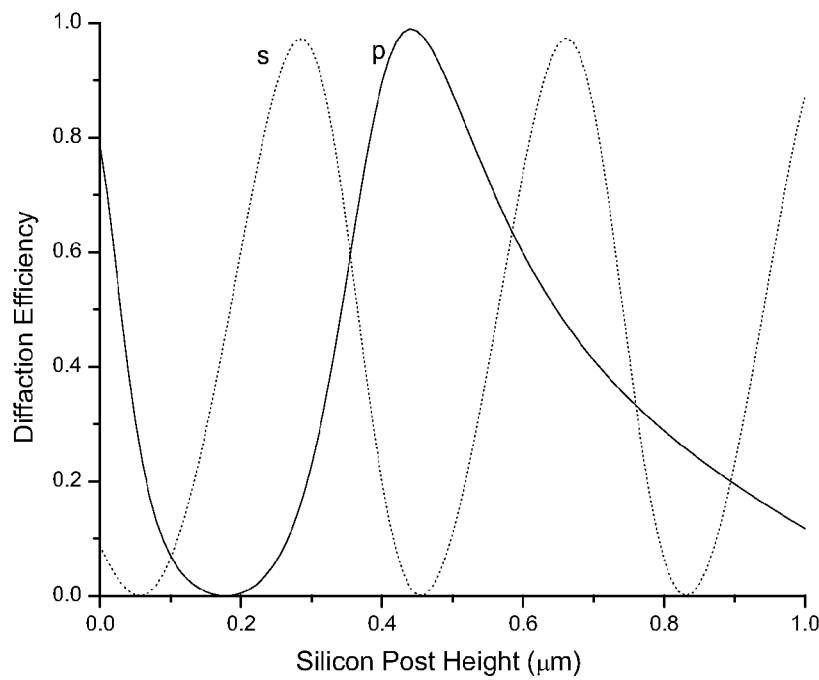

An illustration of such parameter selection is illustrated in FIGS. 9A-9D, which show plots of s- and p-polarized first order diffraction for the device of FIG. 8 as a function of trench depth h for different metal thicknesses t. For each of FIGS. 9A-9D, the grating has a period $\Lambda$=312.5 nm and a duty cycle d/$\Lambda$=0.5. An optical signal with $\lambda$=1545 nm is incident at $\theta_{in}$=45.3° (near-Littrow condition) from the silicon side of the grating. Dotted lines indicate s-polarized first order diffraction efficiency, and solid lines indicate p-polarized first order diffraction efficiency. In FIG. 9A, t=0, i.e., no gold layer is present. Maximum (near unity) first order diffraction efficiency occurs at differing ridge heights h, specifically, about 220 nm for s-polarization and about 500 nm for p-polarization. In FIG. 9B, the gold layer thickness t is 50 nm, resulting in maximal first order diffraction efficiency at ridge heights h of about 280 nm for s-polarization and about 440 nm for p-polarization, closer in wavelength than the grating lacking metal. Note also that a minimum in the s-polarized curve nearly coincides with the maximum in the p-polarized curve at about d=440 nm. An immersion grating fabricated according to those parameters would exhibit polarization selective first order diffraction (i.e., near unity efficiency for p-polarization, near zero efficiency for s-polarization).

Figure 9C:
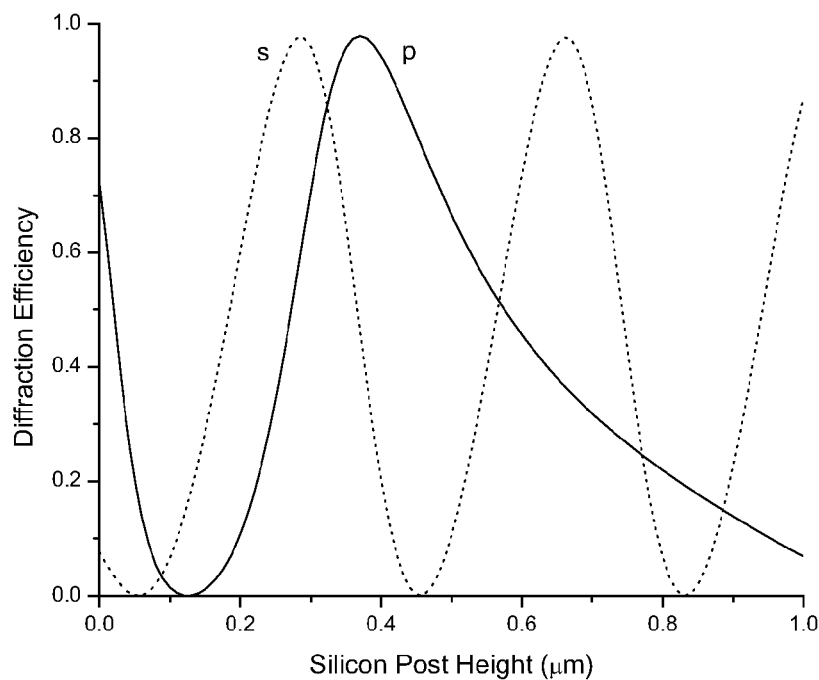
Figure 9D:
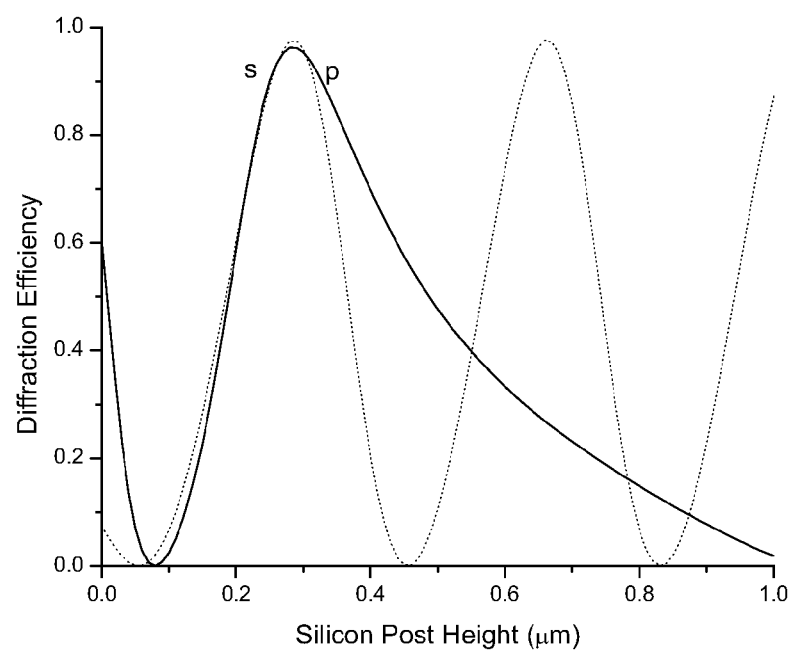
Figure 10:
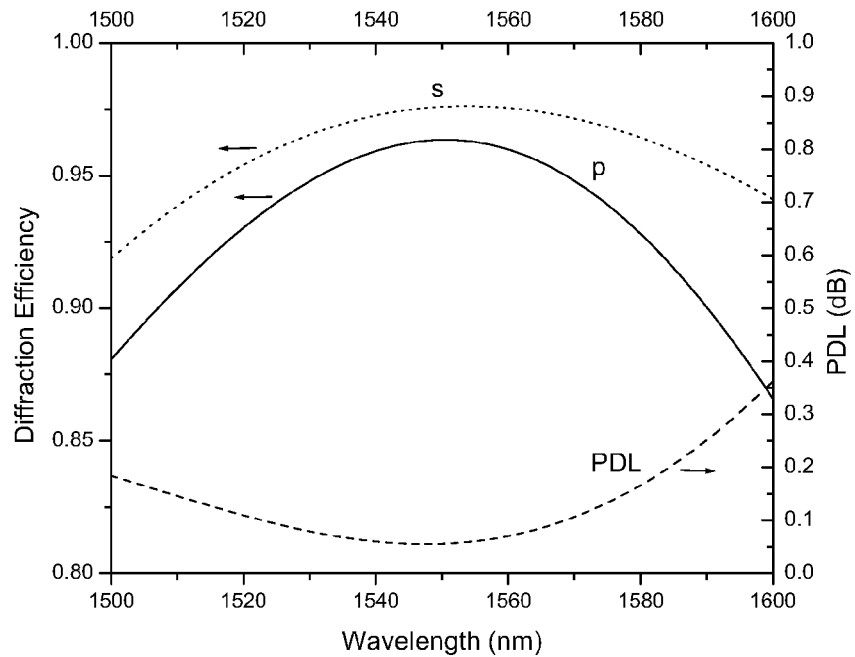
FIG. 10 is a calculated plot of s- and p-polarized first order diffraction efficiency and PDL as a function of wavelength for the grating of FIG. 8.

In FIG. 9C, t=100 nm and the difference in ridge height h that result in maximal first order diffraction efficiency is further decreased, with maximal s-polarized efficiency at h of about 285 nm and maximal p-polarized efficiency at h of about 370 nm. In FIG. 9D, t=150 nm, and maximal first order diffraction efficiencies for s- and p-polarizations substantially coincide at about h=285 nm. An immersion grating fabricated according to those parameters would exhibit reduced, minimal, or no polarization dependence of the first order diffraction (i.e., near unity efficiency for both s- and p-polarization). FIG. 10 shows the first order diffraction efficiency for the grating design of FIG. 9D at a function of wavelength λ for s- (dotted line) and p-polarization (solid line). Greater than 85% efficiency has been calculated for both polarizations over the spectral range shown with less than 0.4 dB polarization-dependent loss (PDL; shown as a dashed line in FIG. 10).

Figure 11:
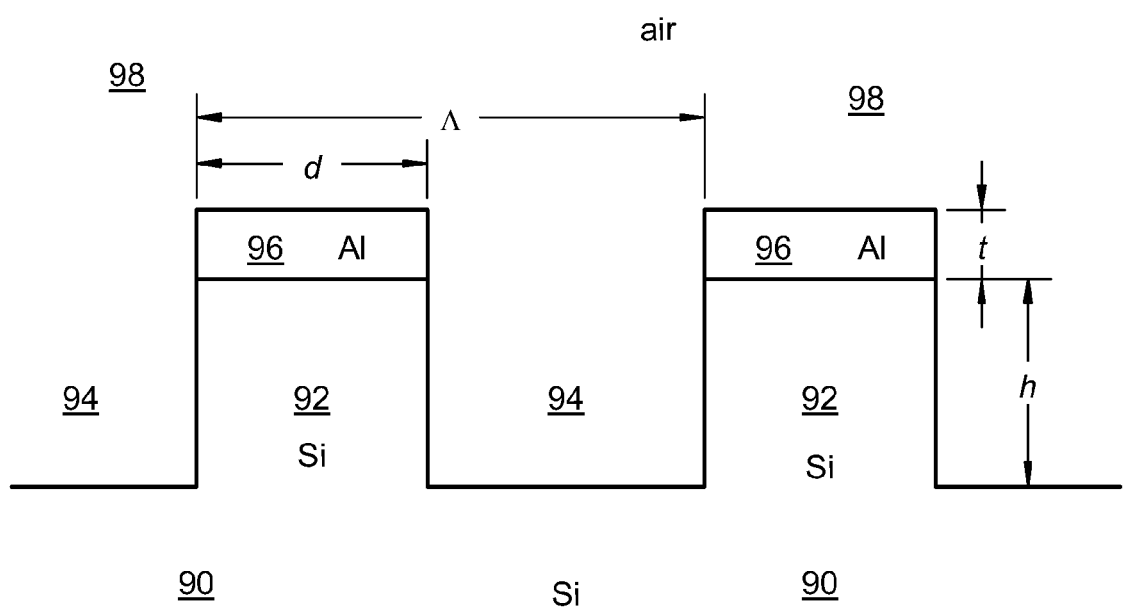
FIG. 11 illustrates schematically another exemplary diffraction grating with a metal layer on each grating ridge.
Figure 12:
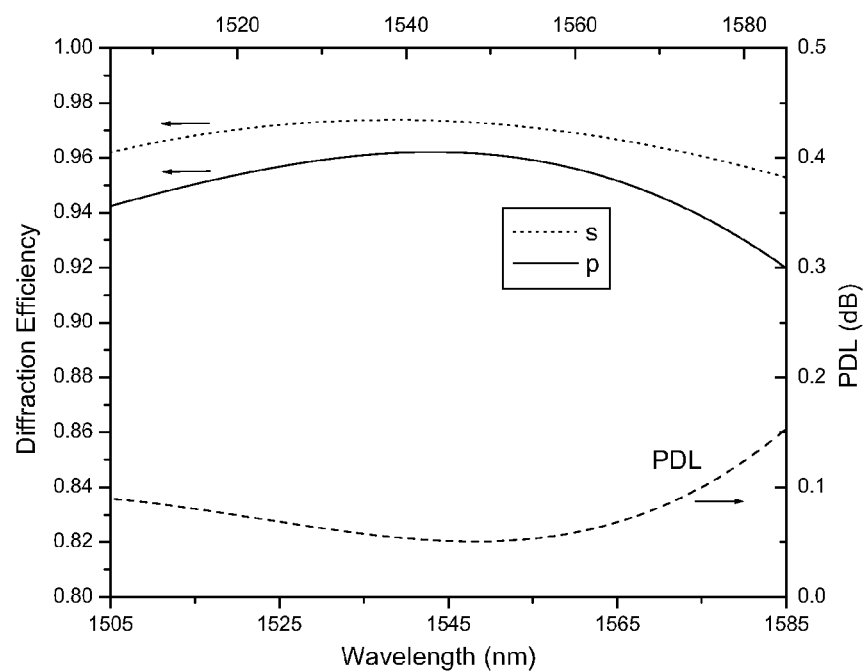
FIG. 12 is a calculated plot of s- and p-polarized first order diffraction efficiency and PDL as a function of wavelength for the grating of FIG. 11.
Figure 13E:
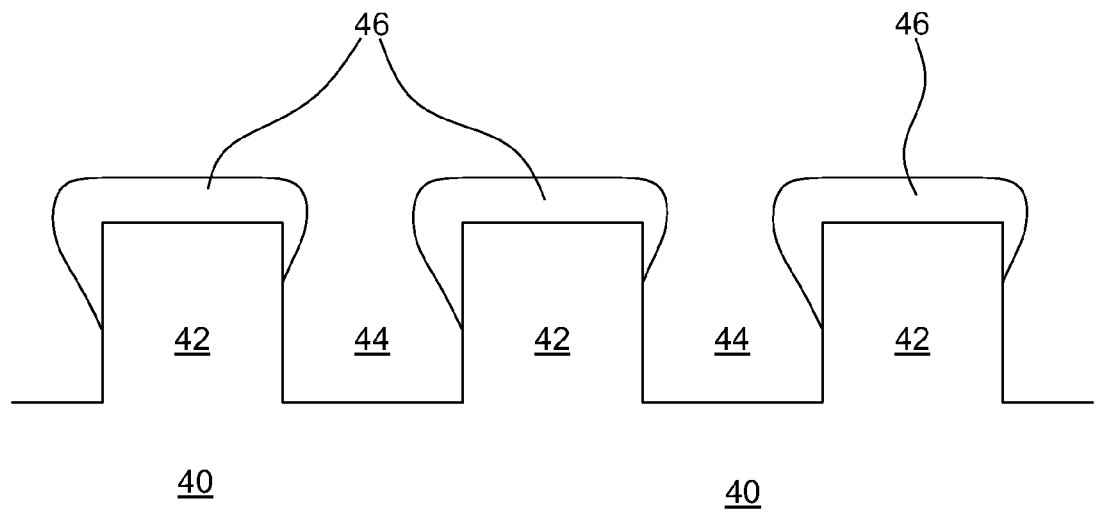
FIG. 13E illustrates schematically an exemplary grating produced by the process of FIGS. 13A-13D.
Figure 14A:
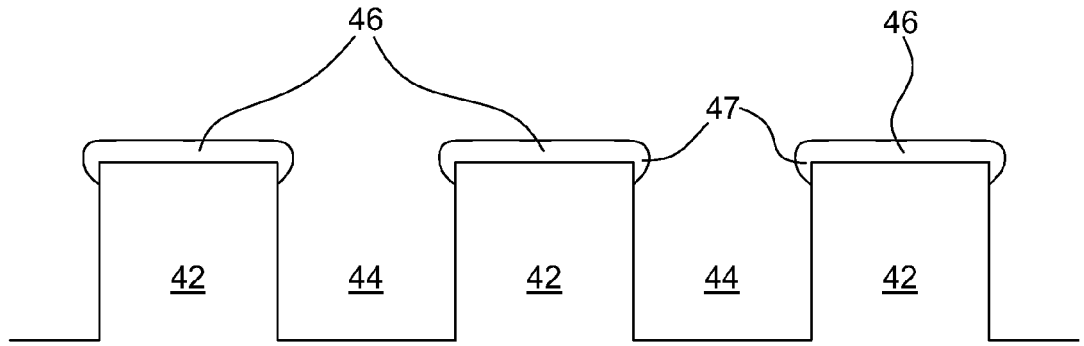
FIGS. 14A-14C illustrate schematically several exemplary diffraction gratings with metal layers on the grating ridges.
Figure 14B:
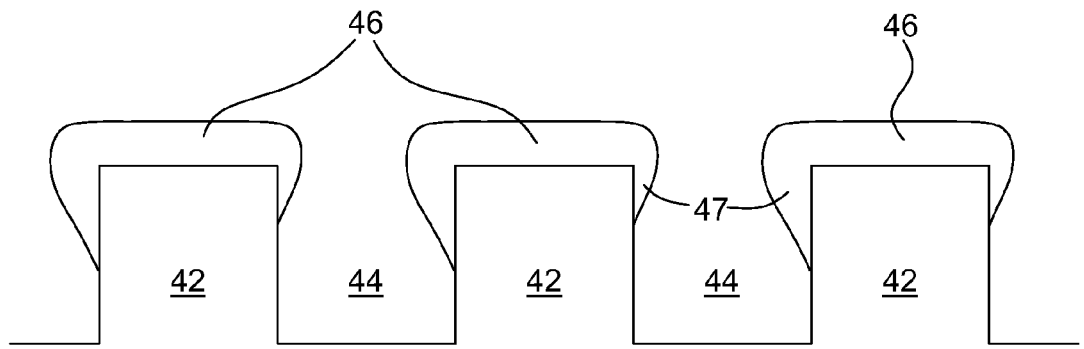
Figure 14C:
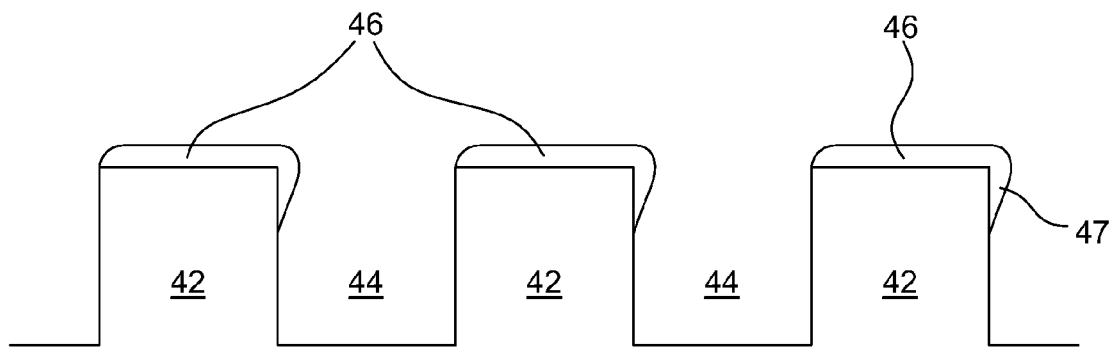

The approach disclosed above for tuning the efficiency or polarization characteristics of an immersion grating is not limited to the use of gold as the metal layer or silicon as the substrate material. Any suitable materials can be employed; examples include but are not limited to gold, silver, aluminum, or other metal for the metal layers, and materials already listed above as the substrate. FIG. 11 illustrates schematically an example wherein the metal layer 96 on the top surface of each ridge 92 comprises aluminum; the bottom surface of each trench 94 is substantially free of metal. The substrate 90 comprises silicon. For the example of FIG. 11, Λ=312.5 nm, the duty cycle d/Λ=0.55, the aluminum layer thickness t is 152 nm, and the silicon ridge height h is 280 nm. FIG. 12 shows the first order diffraction efficiency calculated for the grating design of FIG. 11 for s- (dotted line) and p-polarization (solid line) as a function of wavelength λ from 1505 nm to 1585 nm, indicating a wavelength range over which optical behavior changes only slowly, i.e., the grating efficiencies and polarization dependent (or independent) behaviors remain within operationally acceptable limits. The angle of incidence is $\theta_{in}$=45.3°, (near-Littrow) from the silicon side of the grating. Greater than 90% diffraction efficiency is calculated over the spectral range shown, with less than 0.2 dB polarization-dependent loss over that spectral range (PDL; shown as a dashed line in FIG. 12).

The exemplary values given for $n_1$, $n_2$, Λ, d, h, t, and $\theta_{in}$ are only a few among myriad combinations of values for those parameters that can be employed within the scope of the present invention or appended claims. For example, given a wavelength range and desired diffractive and polarization properties, one or more suitable combinations of those parameters can be selected according to the teachings of the present disclosure by one skilled in the art, based on calculation or experiment, to yield the desired grating behavior.

The fabrication of metal-dielectric or metal-semiconductor immersion grating structures of the general type shown in FIGS. 8 and 11 can proceed via multiple pathways. In a first set of examples, a metal layer of the desired thickness t is deposited onto a substrate, e.g., a lithography-grade silicon wafer. The metal layer is coated with a photoresist (e.g., by spin-coating) that is then patterned with the grating pattern using mask-based photolithography or any other suitable technique. The patterned resist is developed or otherwise processed to form a mask through which the metal layer is etched, e.g., by a dry etch process such as reactive ion etching; any suitable wet or dry etch process or other suitable material removal method can be employed. The grating pattern is thus effectively transferred into the metal layer. In a second etch step, the substrate is etched through the patterned metal layer to the desired depth h thus yielding the required grating ridge height. Using an etch process that preferentially removes the substrate instead of the metal, the patterned metal layer can function as a mask for the substrate patterning. Alternatively, a protective layer can be applied to or remain on the top of the patterned metal, e.g., the residual photoresist from the metal patterning step can serve to prevent, minimize, or reduce metal erosion during the substrate etch.

In a second set of examples, fabrication of metal-dielectric or metal-semiconductor grating structures as disclosed herein comprises using a photoresist for the patterning of the metal layer whose developer removes all developed photoresist and subsequently etches away any metal underlying the developed resist areas. An example is Shipley 151 photoresist, but other suitable resist-developer combinations can be employed. Such a fabrication approach enables fabrication of the immersion grating structures with a reduced number of processing steps.

In another set of examples, the metal layer is deposited on the top surface of each grating ridge after the ridges or grooves are formed on the substrate 40 (e.g., as in FIGS. 13A-13E). The grating ridges 42 or trenches 44 can be formed on the substrate 40 by any suitable spatially selective material processing technique. After the ridges 42 and trenches 44 are formed at the desired ridge height h, the metal layer 46 is applied to the ridge pattern by a directional deposition process, e.g., by vacuum electron-beam evaporation or other suitable directional deposition. FIGS. 13A-13D illustrate schematically an exemplary process that employs an evaporative deposition apparatus 1300; the resulting grating is illustrated schematically in FIG. 13E. To avoid depositing metal on the bottom surfaces of the grooves 44 of the grating, the metal deposition is performed with the substrate 40 oriented at a large enough angle (measured with respect to the normal to the grating substrate 40) so that the groove bottom remains shaded (as in FIGS. 13B and 13D). It is typically the case that such angled deposition also results in a lateral metal layer 47 being formed on an upper portion of one or both side surfaces of each grating ridge (as shown in FIGS. 13B-13E, 14A-14C, and 15A). The metal deposition can be performed at one substrate angle only (e.g., as in FIG. 13B only), or from two or more different angles on opposite sides of the grating substrate normal (e.g., as in both FIGS. 13B and 13D). If performed from angles on opposite sides of the grating substrate normal, the two angles can be the same or can differ (resulting in differing lateral metal layer depths a on opposing sides of the ridges 42), or the amount of metal deposited from each such angle can be the same or can differ (resulting in differing lateral metal layer thicknesses b on opposing sides of the ridges 42). An exemplary deposition process and the resultant metal coating profile are illustrated schematically in FIGS. 13A-13D, in which metal is deposited in two sequential deposition steps, from angles on opposite sides of the grating substrate normal. Depending on the number, magnitude, and orientation of the deposition angles with respect to the grating normal, different cross-sectional metal layer profiles can be created on each grating ridge 42; several examples are illustrated schematically in FIGS. 14A-14C.

The behavior of the immersion grating is influenced by the presence and dimensions of lateral metal coatings 47 on the grating ridges 42. That influence may in some instances be deemed undesirable, and can be avoided, e.g., by etching the grating grooves 44 through a substantially uniform metal layer into the grating substrate 40, thereby forming the ridges 42 and metal layers 46 on each top ridge surface without lateral metal layer 47 (e.g., as in FIGS. 8 and 11). In other instances, the influence of the lateral metal layers 47 may be deemed undesirable but nevertheless tolerated, so as to enable metal deposition, e.g., using a directional deposition process, after forming the ridges 42 or the grooves 44 on the substrate 40. That fabrication sequence may provide advantages in terms of cost or difficulty of the overall fabrication process. In still other instances, the influence of the lateral metal layers 47 can be intentionally employed to provide additional design parameters for an immersion grating.

Figure 15A:
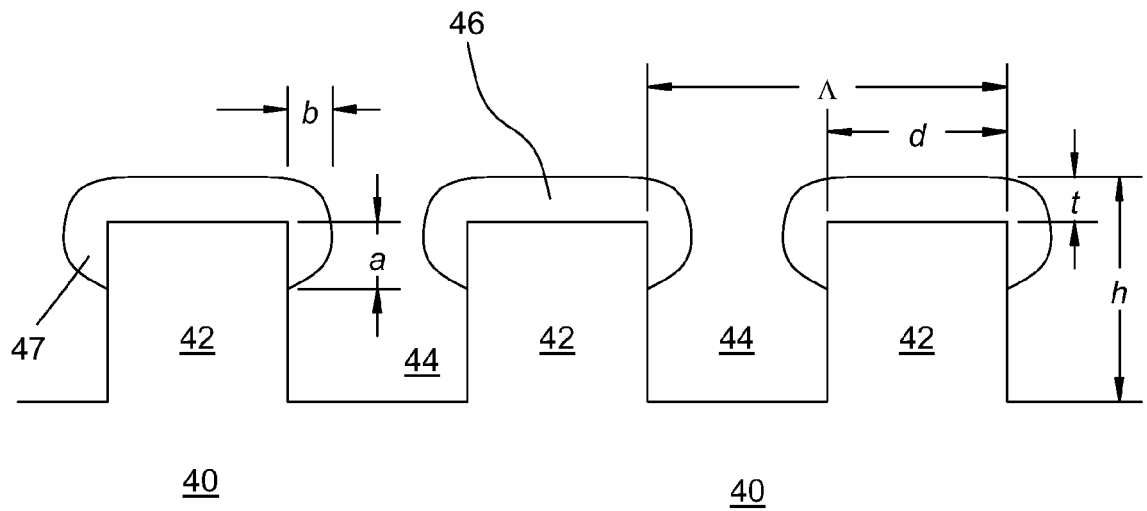
FIG. 15A illustrates schematically an exemplary diffraction grating with metal layers on the gratings ridges.

The dimensions of the metallic layers 46 and 47 (as shown in FIG. 15A; thickness t of the metal layer 46, distance a that the lateral metal layer 47 extends downward from the top surface of the grating ridge 42, and lateral thickness b of the lateral metal layer 47) can be controlled to result in desired optical behavior of the resulting immersion grating. For example, the depth a to which a side surface of each grating ridge 42 is covered by metal layer 47 significantly affect the efficiency or polarization behavior of the immersion grating. An example is illustrated in FIGS. 15A-15C, wherein a silicon grating with period $\Lambda=312.5$ nm, ridge height h=360 nm, duty cycle d/$\Lambda$=0.5, and top aluminum layer thickness t=60 nm has both of its side walls covered with b=25 nm thick aluminum to a depth of a (FIG. 15A). FIGS. 15B and 15C are plots with respect to the depth a of the calculated s- and p-polarized first order diffraction, respectively, of an optical signal at $\lambda=1545$ nm incident from within the silicon substrate at an angle of incidence $\theta_{in}=45.3°$ (near-Littrow). The first order diffraction efficiency for p-polarized optical input depends relatively weakly on the depth a over most of the range shown in FIG. 15C. The s-polarized first order diffraction efficiency exhibits a stronger dependence on a and varies between >90% and about 10% over the same range of a.

The side wall coating depth a may thus be adjusted to design and fabricate gratings having first order diffraction efficiency that is relatively polarization dependent or independent, as needed or desired. As shown in FIGS. 13A-13E, the depth a to which the sidewall of each grating ridge 42 is coated is substantially determined by the chosen substrate angle used during metal deposition. The thicknesses t and b are determined by the amount of metal deposited (i.e., by the rate and duration of the deposition process), and are constrained to be related to one another according to the deposition angle. Just as the metal layer 46 might not be uniform, the metal deposition processes used to form the metal layers 46 and 47 may not yield a lateral metal layer 47 of uniform thickness. Such non-uniform layers nevertheless result in the behavior disclosed herein, and shall fall within the scope of the present disclosure or appended claims. In the case of a non-uniform lateral metal layer 47, the thickness b that characterizes the layer can be an average thickness or a maximum thickness, for example.

Figure 16:
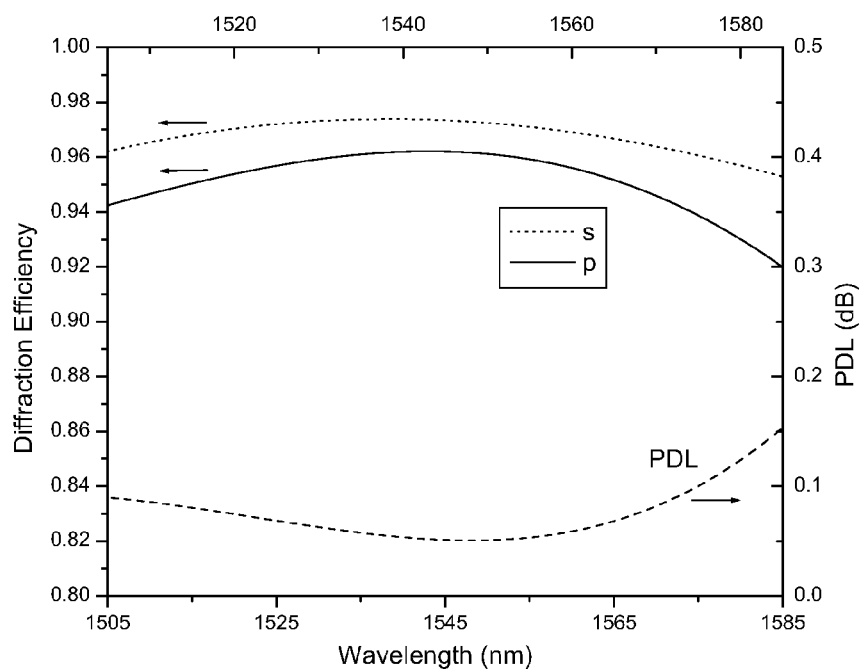
FIG. 16 is a calculated plot of s- and p-polarized first order diffraction efficiency as a function of wavelength for the grating of FIG. 15A.

FIG. 16 shows the first order diffraction efficiency calculated for both s- and p-polarizations as a function of wavelength $\lambda$ for a relatively polarization-insensitive grating design for both polarizations as a function of wavelength. In that example, the grating parameters are those of FIGS. 15A-15B, with the sidewall coating depth a=115 nm (i.e., near the maximum first order diffraction efficiency for s-polarization in FIG. 15B). Over the spectral range shown the diffraction efficiency difference between the two polarizations is less than 4% and the absolute diffraction efficiency remains greater than 90%. Overall diffraction efficiency of up to about 85% and PDL less than about 0.5 dB over a wavelength range of 1520-1580 nm has been measured for gratings fabricated according to the process of FIGS. 13A-13D.

In some examples, the depth a of the lateral metal layer 47 might be substantially equal to the ridge height h, i.e., the lateral metal layer 47 might reach the bottom of the trench 44, or even extend partially onto the bottom of the trench 44. In such embodiments, at least a portion of the bottom of the trench shall nevertheless remain substantially free of metal, and such embodiments shall fall within the scope of the present disclosure or appended claims.

The exemplary values given for $n_1$, $n_2$, $\Lambda$, d, h, t, a, b, and $\theta_{in}$ are only a few among myriad combinations of values for those parameters that can be employed within the scope of the present invention or appended claims. For example, given a wavelength range and desired diffractive and polarization properties, one or more suitable combinations of those parameters can be selected according to the teachings of the present disclosure by one skilled in the art, based on calculation or experiment, to yield the desired grating behavior.

Generally, operationally acceptable grating performance can include performance in terms of diffraction efficiency and polarization-dependent loss such as those shown in FIGS. 4B, 5B, 6A, 6B, 7, 9A-9D, 10, 12, 15B, 15C, and 16. However, immersion gratings disclosed or claimed herein should not be viewed as limited to such values. Rather, different uses of an optical grating may have more or less stringent requirements for grating performance, or more or less restrictive constraints based on ease or cost of fabrication, and the term operationally acceptable performance is defined in the context of the relevant use.

While the exemplary gratings disclosed herein have been described primarily in the context of use as immersion gratings under conditions of total internal reflection and only a single permitted diffractive order, it should be understood that gratings fabricated as disclosed or claimed herein (e.g., with a metal layer on each grating ridge top and at least a portion of each grating trench bottom substantially free of metal, also possibly including lateral metal layers) can be employed in other arrangements that permit multiple diffraction orders or transmitted diffraction orders.

It is intended that equivalents of the disclosed exemplary embodiments and methods shall fall within the scope of the present disclosure or appended claims. It is intended that the disclosed exemplary embodiments and methods, and equivalents thereof, may be modified while remaining within the scope of the present disclosure or appended claims.

In the foregoing Detailed Description, various features may be grouped together in several exemplary embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed exemplary embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., sets of features that are not incompatible or mutually exclusive) that appear in the present disclosure or the appended claims, including those sets of one or more features that may not be explicitly disclosed herein. It should be further noted that the scope of the appended claims do not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure or appended claims, the words "comprising," "including," "having," and variants thereof, wherever they appear, shall be construed as open ended terminology, with the same meaning as if the phrase "at least" were appended after each instance thereof.

In the appended claims, if the provisions of 35 USC §112 ¶ 6 are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC §112 ¶ 6 are not intended to be invoked for that claim.

What is claimed is:

1. A diffraction grating comprising:
a substrate comprising a first dielectric or semiconductor material substantially transparent over a range of operational wavelengths $\lambda$ with a refractive index $n_1$, and having a first surface facing an optical medium with a refractive index $n_2$ that is less than $n_1$;
a set of diffractive elements formed on the first surface of the substrate, wherein the diffractive elements comprise a set of protruding ridges separated by intervening trenches characterized by a ridge spacing $\Lambda$, a ridge width d, and a ridge height h; and
a metal layer on a to surface of each ridge characterized by a thickness t,
wherein:
at least a portion of a bottom surface of each trench is substantially free of metal;
$\lambda/2n_1 < \Lambda < \lambda/(n_1+n_2)$ over the operational wavelength range; and
$n_1$, $n_2$, $\Lambda$, d, h, and t result in wavelength dependent diffraction efficiency over the operational wavelength range for s- and p-polarized optical signals wherein (i) a minimum of the p-polarized diffraction efficiency substantially coincides with a maximum of the s polarized diffraction efficiency or (ii) a maximum of the p-polarized diffraction efficiency substantially coincides with a minimum of the s-polarized diffraction efficiency, so that overall diffraction efficiency is polarization selective over the operational wavelength range for an optical signal incident on the diffractive elements from within the substrate at an incidence angle $\theta_{in}$ that exceeds a critical angle $\theta_c = \sin^{-1}(n_2/n_1)$.

2. The diffraction grating of claim 1 wherein a polarization ratio of the polarization selective diffraction efficiency is greater than about 100:1, and the operational wavelength range is about 1500 nm to about 1600 nm.

3. The diffraction grating of claim 1 wherein the substrate comprises a prism having a second surface that is not parallel to the first surface, wherein the first and second surfaces are arranged so that an optical signal transmitted through the first surface is incident on the diffractive elements from within the substrate at an incidence angle $\theta_{in}$ that exceeds a critical angle $\theta_c = \sin^{-1}(n_2/n_1)$.

4. The diffraction grating of claim 1 wherein:
the substrate is arranged so as to receive an optical signal in the operational wavelength range that is incident on the diffractive elements from within the substrate at an incidence angle $\theta_{in}$ that exceeds a critical angle $\theta_c = \sin^{-1}(n_2/n_1)$; and
$n_1$, $n_2$, $\Lambda$, and $\theta_{in}$ result in near-Littrow diffraction of the optical signal.

5. The diffraction grating of claim 1 wherein the first material comprises optical glass, fused silica, silicon, silicon nitride, or silicon oxynitride, and the optical medium comprises vacuum, air, a gaseous medium, or a liquid medium.

6. The diffraction grating of claim 1 wherein the metal comprises gold, silver, or aluminum.

7. A diffraction grating comprising:
a substrate comprising a first dielectric or semiconductor material substantially transparent over a range of operational wavelengths $\lambda$ with a refractive index $n_1$, and having a first surface facing an optical medium with a refractive index $n_2$ that is less than $n_1$;
a set of diffractive elements formed on the first surface of the substrate, wherein the diffractive elements comprise a set of protruding ridges separated by intervening trenches characterized by a ridge spacing $\Lambda$, a ridge width d, and a ridge height h; and
a metal layer on a to surface of each ridge characterized by a thickness t,
wherein:
at least a portion of a bottom surface of each trench is substantially free of metal;
$\lambda/2n_1 < \Lambda < \lambda/(n_1+n_2)$ over the operational wavelength range; and
$n_1$, $n_2$, $\Lambda$, d, h, and t result in wavelength dependent diffraction efficiency over the operational wavelength range for s- and p-polarized optical signals wherein a maximum of the p-polarized diffraction efficiency substantially coincides with a maximum of the s-polarized diffraction efficiency, so that polarization dependent loss PDL is less than a prescribed level over the operational wavelength range for an optical signal incident on the diffractive elements from within the substrate at an incidence angle $\theta_{in}$ that exceeds a critical angle $\theta_c = \sin^{-1}(n_2/n_1)$.

8. The diffraction grating of claim 7 wherein the prescribed level of polarization dependent loss is about 0.5 dB and the operational wavelength range is about 1500 nm to about 1600 nm.

9. The diffraction grating of claim 7 wherein the substrate comprises a prism having a second surface that is not parallel to the first surface, wherein the first and second surfaces are arranged so that an optical signal transmitted through the first surface is incident on the diffractive elements from within the substrate at an incidence angle $\theta_{in}$ that exceeds a critical angle $\theta_c = \sin^{-1}(n_2/n_1)$.

10. The diffraction grating of claim 7 wherein:
the substrate is arranged so as to receive an optical signal in the operational wavelength range that is incident on the diffractive elements from within the substrate at an incidence angle $\theta_{in}$ that exceeds a critical angle $\theta_c = \sin^{-1}(n_2/n_1)$; and
$n_1$, $n_2$, $\Lambda$, and $\theta_{in}$ result in near-Littrow diffraction of the optical signal.

11. The diffraction grating of claim 7 wherein the first material comprises optical glass, fused silica, silicon, silicon nitride, or silicon oxynitride, and the optical medium comprises vacuum, air, a gaseous medium, or a liquid medium.

12. The diffraction grating of claim 7 wherein the metal comprises gold, silver, or aluminum.

13. A diffraction grating comprising:
a substrate comprising a first dielectric or semiconductor material substantially transparent over a range of operational wavelengths $\lambda$ with a refractive index $n_1$, and having a first surface facing an optical medium with a refractive index $n_2$ that is less than $n_1$;
a set of diffractive elements formed on the first surface of the substrate, wherein the diffractive elements comprise a set of protruding ridges separated by intervening trenches characterized by a ridge spacing $\Lambda$, a ridge width d, and a ridge height h;
a metal layer on a top surface of each ridge characterized by a thickness t; and
a lateral metal layer on at least one side surface of each ridge, wherein each lateral metal layer extends a distance a downward from the top surface of the corresponding ridge and is characterized by a lateral thickness b,
wherein:
at least a portion of a bottom surface of each trench is substantially free of metal;
$\lambda/2n_1 < \Lambda < \lambda/(n_1+n_2)$ over the operational wavelength range; and
$n_1$, $n_2$, $\Lambda$, d, h, t, a, and b result in wavelength dependent diffraction efficiency over the operational wavelength range for s- and p-polarized optical signals wherein a maximum of the p-polarized diffraction efficiency substantially coincides with a maximum of the s-polarized diffraction efficiency, so that polarization dependent loss PDL is less than a prescribed level over the operational wavelength range for an optical signal incident on the diffractive elements from within the substrate at an incidence angle $\theta_{in}$ that exceeds a critical angle $\theta_c = \sin^{-1}(n_2/n_1)$.

14. The diffraction grating of claim 13 wherein the prescribed level of polarization dependent loss is about 0.5 dB and the operational wavelength range is about 1500 nm to about 1600 nm.

15. The diffraction grating of claim 13 wherein the substrate comprises a prism having a second surface that is not parallel to the first surface, wherein the first and second surfaces are arranged so that an optical signal transmitted through the first surface is incident on the diffractive elements from within the substrate at an incidence angle $\theta_{in}$ that exceeds a critical angle $\theta_c = \sin^{-1}(n_2/n_1)$.

16. The diffraction grating of claim 13 wherein:
the substrate is arranged so as to receive an optical signal in the operational wavelength range that is incident on the diffractive elements from within the substrate at an incidence angle $\theta_{in}$ that exceeds a critical angle $\theta_c = \sin^{-1}(n_2/n_1)$; and
$n_1$, $n_2$, $\Lambda$, and $\theta_{in}$ result in near-Littrow diffraction of the optical signal.

17. The diffraction grating of claim 13 wherein the first material comprises optical glass, fused silica, silicon, silicon nitride, or silicon oxynitride, and the optical medium comprises vacuum, air, a gaseous medium, or a liquid medium.

18. The diffraction grating of claim 13 wherein the metal comprises gold, silver, or aluminum.

19. A method for forming a diffraction grating comprising:
forming a set of diffractive elements on a first surface of a substrate, wherein the diffractive elements comprise a set of protruding ridges separated by intervening trenches; and
forming a metal layer on a top surface of each ridge,
wherein:
the substrate comprises a first dielectric or semiconductor material substantially transparent over a range of operational wavelengths $\lambda$ with a refractive index $n_1$, and the first surface faces an optical medium with a refractive index $n_2$ that is less than $n_1$;
the set of diffractive elements is characterized by a ridge spacing $\Lambda$, a ridge width d, and a ridge height h;
the metal layer is characterized by a thickness t;
at least a portion of a bottom surface of each trench is substantially free of metal;
$\lambda/2n_1 < \Lambda < \lambda/(n_1+n_2)$ over the operational wavelength range; and
$n_1$, $n_2$, $\Lambda$, d, h, and t result in wavelength dependent diffraction efficiency over the operational wavelength range for s- and p-polarized optical signals wherein (i) a minimum of the p-polarized diffraction efficiency substantially coincides with a maximum of the s-polarized diffraction efficiency or (ii) a maximum of the p-polarized diffraction efficiency substantially coincides with a minimum of the s-polarized diffraction efficiency, so that overall diffraction efficiency is polarization selective over the operational wavelength range for an optical signal incident on the diffractive elements from within the substrate at an incidence angle $\theta_{in}$ that exceeds a critical angle $\theta_c = \sin^{-1}(n_2/n_1)$.

20. The method of claim 19 wherein forming the diffractive elements and the metal layers comprises spatially-selectively etching the trenches through a substantially uniform metal layer on the first substrate surface and into the substrate, thereby forming the ridges between the trenches and leaving the metal layers on the top surface of each ridge.

21. The method of claim 20 further comprising depositing the substantially uniform metal layer on the first substrate surface prior to etching the trenches.

22. The method of claim 19 wherein forming the metal layers comprises depositing metal on the top surface of each ridge after the ridges are formed.

23. The method of claim 22 wherein metal is deposited on the top surface of each ridge by directional deposition at one or more deposition angles that substantially block deposition of metal on at least a portion of the bottom surface of each trench.

24. A method for forming a diffraction grating comprising:
forming a set of diffractive elements on a first surface of a substrate, wherein the diffractive elements comprise a set of protruding ridges separated by intervening trenches; and
forming a metal layer on a top surface of each ridge,
wherein:
the substrate comprises a first dielectric or semiconductor material substantially transparent over a range of operational wavelengths $\lambda$ with a refractive index $n_1$ and the first surface faces an optical medium with a refractive index $n_2$ that is less than $n_1$;
the set of diffractive elements is characterized by a ridge spacing $\Lambda$, a ridge width d, and a ridge height h;
the metal layer is characterized by a thickness t;
at least a portion of a bottom surface of each trench is substantially free of metal;

$\lambda/2n_1 < \Lambda < \lambda/(n_1+n_2)$ over the operational wavelength range; and $n_1$, $n_2$, $\Lambda$, d, h, and t result in wavelength dependent diffraction efficiency over the operational wavelength range for s- and p-polarized optical signals wherein a maximum of the p-polarized diffraction efficiency substantially coincides with a maximum of the s-polarized diffraction efficiency, so that polarization dependent loss PDL is less than a prescribed level over the operational wavelength range for an optical signal incident on the diffractive elements from within the substrate at an incidence angle $\theta_{in}$ that exceeds a critical angle $\theta_c = \sin^{-1}(n_2/n_1)$.

25. The method of claim 24 wherein forming the diffractive elements and the metal layers comprises spatially-selectively etching the trenches through a substantially uniform metal layer on the first substrate surface and into the substrate, thereby forming the ridges between the trenches and leaving the metal layers on the top surface of each ridge.

26. The method of claim 25 further comprising depositing the substantially uniform metal layer on the first substrate surface prior to etching the trenches.

27. The method of claim 24 wherein forming the metal layers comprises depositing metal on the top surface of each ridge after the ridges are formed.

28. The method of claim 27 wherein metal is deposited on the top surface of each ridge by directional deposition at one or more deposition angles that substantially block deposition of metal on at least a portion of the bottom surface of each trench.

29. A method for forming a diffraction grating comprising:
forming a set of diffractive elements on a first surface of a substrate, wherein the diffractive elements comprise a set of protruding ridges separated by intervening trenches;
forming a metal layer on a top surface of each ridge; and
forming a lateral metal layer on at least one side surface of each ridge,
wherein:
the substrate comprises a first dielectric or semiconductor material substantially transparent over a range of operational wavelengths $\lambda$ with a refractive index $n_1$, and the first surface faces an optical medium with a refractive index $n_2$ that is less than $n_1$;
the set of diffractive elements is characterized by a ridge spacing $\Lambda$, a ridge width d, and a ridge height h;
the metal layer is characterized by a thickness t;
each lateral metal layer extends a distance a downward from the top surface of the corresponding ridge and is characterized by a lateral thickness b;
at least a portion of a bottom surface of each trench is substantially free of metal; and
$\lambda/2n_1 < \Lambda < \lambda/(n_1+n_2)$ over the operational wavelength range, and wherein $n_1$, $n_2$, $\Lambda$, d, h, t, a, and b result in wavelength dependent diffraction efficiency over the operational wavelength range for s- and p-polarized optical signals wherein a maximum of the p-polarized diffraction efficiency substantially coincides with a maximum of the s-polarized diffraction efficiency, so that polarization dependent loss PDL is less than a prescribed level over the operational wavelength range for an optical signal incident on the diffractive elements from within the substrate at an incidence angle $\theta_{in}$ that exceeds a critical angle $\theta_c = \sin^{-1}(n_2/n_1)$.

30. The method of claim 29 wherein the metal layers are deposited on the top surface of each ridge, after the ridges are formed, by directional deposition at one or more deposition angles that substantially block deposition of metal on the bottom surface of each trench and result in the lateral metal layers that extend the distance a downward from the top surface of the corresponding ridge and are characterized by the lateral thickness b.

\* \* \* \* \*